Sept. 10, 1963 A. MEILLAND Plant Pat. 2,283
ROSE PLANT
Filed Sept. 5, 1962
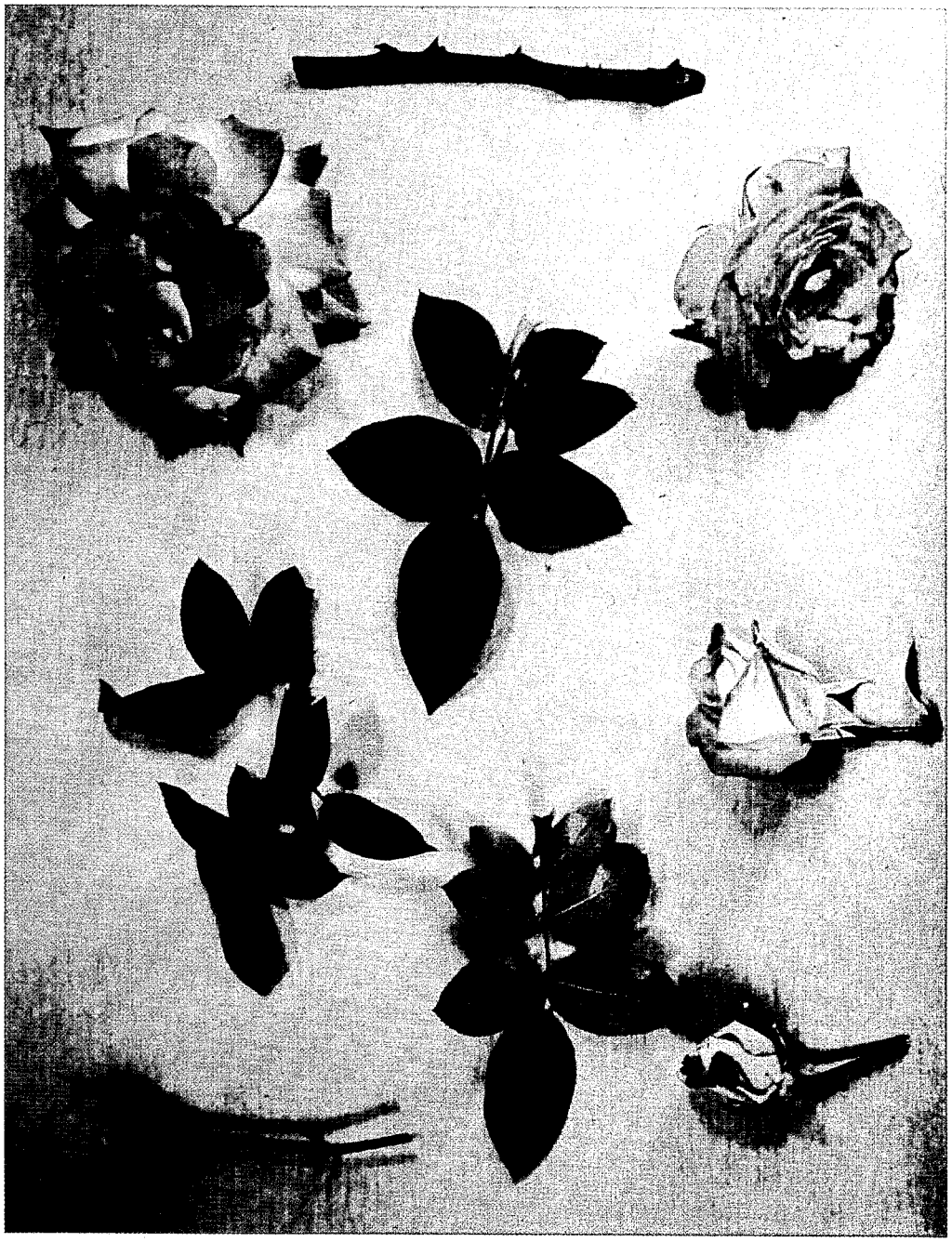
Inventor.
Alain Meilland
By: Robb & Robb
Attorneys.

United States Patent Office

Plant Pat. 2,283
Patented Sept. 10, 1963

2,283
ROSE PLANT

Alain Meilland, Cap d'Antibes, Alpes-Maritimes, France, assignor to The Conard-Pyle Company, West Grove, Pa., a corporation of Pennsylvania Filed Sept. 5, 1962, Ser. No. 221,640
Claims priority, application France Mar. 9, 1962
1 Claim. (Cl. Plt.—11)

The present invention relates to a new and distinct variety of rose plant of the hybrid tea class, which was originated by me by crossing the variety known as "Baccara" (U.S. Plant Patent No. 1,367) with an unnamed and unpatented first generation seedling derived from a cross of the variety "Kordes' Sondermeldung," known in the United States as "Independence" (U.S. Plant Patent No. 1,036 × "Grand'mere Jenny" (U.S. Plant Patent No. 1,148).

The primary objective of this breeding was to create a new rose variety which produces flowers having a more sharp and intense color contrast than in those of the variety "Grand'mere Jenny." In carrying out this objective, I endeavored to breed into the new variety the red flower colors of the varieties "Kordes' Sondermeldung" and "Baccara." My objective was thus fully achieved, along with other desirable improvements, as evidenced by the following unique combination of characteristics which are outstanding in the new variety and which distinguish it from its parents, as well as from all other varieties of which I am aware:

(1) A semi-double flower form;

(2) Wide flower petals;

(3) An unusual and original bicolor decorative effect of red and white colors which persist from the opening of the buds to the fully open flower stage;

(4) A distinctive marking of the inside of the flower petals with a wide red aureole extending over half their surface and blending to white over the basal half which terminates in a yellow basal tip; and (5) A distinctive and striking Spirea Red color, shading with Ruby Red in the full open, aging flower stage.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—"Baccara."

*Pollen parent.*—An unnamed seedling of "Kordes' Sondermeldung" ("Independence" in the United States) × "Grand'mere Jenny."

Propagation: Holds its distinguishing characteristics through succeeding propagations by budding.

*Flower*

Locality where grown and observed: West Grove, Pennsylvania, U.S.A.

Flowers borne: Usually several to stem; on stems of medium length and normal strength.

Quantity of bloom: Free, outdoors.

Continuity: Continuous.

Fragrance: Slight. Nature—tea.

Bud:

*Peduncle.*—Medium length; medium thickness; erect; stiff; rough; with numerous hairs. Color—Lettuce Green, Plate 861, usually overlaid with Oxblood Red, Plate 00918.

*Before calyx breaks.*—Size—medium. Form—medium length; pointed-ovoid; with a conspicuous neck; with foliaceous appendages on the surface of the bud; with bristle-like foliaceous parts extending beyond the tip of the bud equal to ¼ of its length.

*As calyx breaks.*—Color—Delft Rose, Plate 020 on first breaking, becoming Purple Madder, Plate 1028 where first exposed to sunlight.

*As first petal opens.*—Size—medium. Form—medium length; pointed-ovoid. Color: outside—near Mimosa Yellow, Plate 602/1 at base of petal and extending over areas protected from sunlight, becoming overlaid with Geranium Lake, Plate 20/2 where newly exposed to light and sharply marked with Purple Madder, Plate 1028 where first exposed to sunlight; inside—Sulphur Yellow, Plate 1, at base of petal, becoming tinted with Sulphur Yellow, Plate 1/2 over main body of petal, broadly margined with slightly darker than Cherry, Plate 722.

*Opening.*—Opens up well.

Bloom:

*Size (when fully open).*—From medium to large; from 4½ inches to 4¾ inches.

*Petalage.*—Semi-double; from 30 to 35 petals; arranged regularly.

*Form.*—Cupped at first and becoming shallow-cupped; petals at first being loosely rolled outward and remaining loosely rolled outward at maturity.

Petals:

*Texture.*—Medium thickness. Inside—satiny. Outside—shiny.

*Shape.*—Outer—obovate. Intermediate — obovate. Inner—irregular.

This description of a newly opened flower was made from a rose grown outdoors during the month of October at West Grove, Pennsylvania, U.S.A.:

*Color.*—Outer petal: Outside surface—white over main body of petal, becoming stippled with Spirea Red, Plate 025/1 towards margin, with edge of petals margined with Spirea Red, Plate 025/1; inside surface—Sulphur Yellow, Plate 1/3 at base, grading to white over basal quarter of petal, becoming stippled with Spirea Red, Plate 025 and very broadly margined with Rose Red, Plate 724 to the edge of the petal. Intermediate petal: outside surface—white over main body of the petal, becoming progressively suffused with and stippled with Spirea Red, Plate 025/1 toward edge of petal; inside surface—Sulphur Yellow, Plate 1/2 at base of petal, surrounded by a zone of white which becomes stippled with Spirea Red, Plate 025/1 and then overlaid with Spirea Red, Plate 025 to form a broad margin over the upper half of the petal. Inner petal: outside surface—white over main body of petal, becoming progressively stippled with Spirea Red, Plate 025/1, and terminating at apex of petal with Spirea Red, Plate 025; inside surface—Sulphur Yellow, Plate 1/2 at base of petal, becoming progressively stippled and overlaid with Spirea Red, Plate 025 toward apex of petal.

This description was made from a rose that was open for three days outdoors during the month of October at West Grove, Pennsylvania, U.S.A.:

*Color.*—Outer petal: outside surface—white at base of petal, overlaid with Spirea Red, Plate 025/2 where exposed to light, and shaded with area of Ruby Red, Plate 827/2 where first exposed to sunlight; inside surface—Sulphur Yellow, Plate 1/3 at base of petal, becoming white and then progressively suffused and overlaid with Spirea Red, Plate 025 over upper half of petal. Inner petal: outside surface—white at base of petal, becoming suffused and overlaid with Magenta Rose, Plate 027/1 over upper half of petal; inside surface—near Magenta, Plate 27/2 at base and over lower half of petal, grading to Spirea Red, Plate 025, overlaid with Ruby Red, Plate 827.

*General color effect.*—Newly opened flower—white at center of petals, surrounded by broad margin of Spirea Red, Plate 025. 3-days open—Spirea Red, Plate 025 shaded with Ruby Red, Plate 827.

*Behavior.*—Drop off cleanly.

*Flower longevity.*—On bush in garden—4 days during October. Cut roses grown outdoors and kept at living room temperatures—4 days during October.

*Reproductive Organs*

Stamens: Medium number; arranged irregularly about pistils.

Filaments: Many; most with anthers; medium length. Color—Mimosa Yellow, Plate 602/1 at base, grading to Delft Rose, Plate 020/1 toward tips.

Anthers: Open at various times; medium size; occasionally an anther fused with a petaloid. Color—Aureolin, Plate 3/1.

Pollen: Moderate quantity. Color—gold.

Pistils: Medium number.

Styles: Uneven; medium length; medium caliper; bunched.

Stigma: Color—white-yellow.

Ovaries: All enclosed in receptacle.

Hips: None observed.

Sepals: Permanent; medium length; spear-shaped.

Seeds: None observed.

*Plant*

Foliage:

*Leaves.*—Usually compound of 3 or 5 leaflets; normal abundance; medium size; leathery.

*Leaflets.*—Shape—oval, with apex acute. Base—obtuse. Margin—simply serrate.

*Color.*—Mature: upper surface—Ivy Green, Plate 0001060; under surface—near Lavender Green, Plate 000761. Young: upper surface—near Maroon, Plate 1030, overlying Parsley Green, Plate 00962; under surface—near Beetroot Purple, Plate 830/1, overlying Parsley Green, Plate 00962/3.

*Rachis (the supporting stem of the compound leaf).*—Medium size. Upper side—grooved; hairy. Under side—sparsely prickly.

*Stipules.*—Medium length; medium width; with short points turning out at an angle of generally less than 45°.

*Disease resistance.*—Comparable to that of the average variety grown under the same cultural conditions at West Grove, Pennsylvania, U.S.A.

Growth:

*Habit.*—Bushy; much-branched.

*Growth.*—Free.

*Canes.*—Medium caliper.

*Main stems.*—Bright. Color—slightly darker than Lettuce Green, Plate 861. Prickles—several; color—somewhat lighter than Garnet Brown, Plate 00918/3. Hairs—none.

*Branches.*—Bright. Color—near Lettuce Green, Plate 861. Prickles—several; color—near Fern Green, Plate 0862/3, lightly overlaid with Garnet Brown, Plate 00918/3 toward the point. Hairs—few; color—near Fern Green, Plate 0862/3.

*New shoots.*—Dull. Color—near Garnet Brown, Plate 00918, overlying Fern Green, Plate 0862. Prickles—several; color—near Garnet Brown, Plate 00918. Hairs—few; color—near Garnet Brown, Plate 00918.

I claim:

A new and distinct variety of rose plant of the hybrid tea class, substantially as herein shown and described, characterized particularly as to novelty by the unique combination of a semi-double flower form, wide flower petals, a distinctive and original bicolor decorative effect of red and white colors which persist from the opening of the buds to the full open flower stage, with the flower petals marked on their inner surfaces with a wide red aureole extending over half their surface and with the basal half of the inner petal surfaces being white with a yellow basal tip, and the general color tonality of the flowers in their fully open aging stage being Spirea Red, shaded with Ruby Red.

No references cited.